United States Patent
Khatib

(10) Patent No.: US 8,647,819 B2
(45) Date of Patent: Feb. 11, 2014

(54) ASSOCIATION OF THE PROGESTERONE RECEPTOR WITH FERTILITY

(75) Inventor: Hasan Khatib, Fitchburg, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 345 days.

(21) Appl. No.: 12/946,865

(22) Filed: Nov. 16, 2010

(65) Prior Publication Data

US 2011/0118539 A1     May 19, 2011

Related U.S. Application Data

(60) Provisional application No. 61/261,377, filed on Nov. 16, 2009.

(51) Int. Cl.
*C12Q 1/68* (2006.01)
*A61B 17/43* (2006.01)

(52) U.S. Cl.
USPC ............ 435/6.1; 435/6.11; 435/6.12; 600/33; 600/34

(58) Field of Classification Search
None
See application file for complete search history.

(56) References Cited

U.S. PATENT DOCUMENTS

2009/0216074 A1*   8/2009   Khatib et al. .................. 600/35

OTHER PUBLICATIONS

Driver et al. J. Dairy Sci. 92 :4082-4085; 2009.*
Khatib et al. 2008 J. Dairy Sci. 91:784-793.*
Bos taurus clone CH240-198D21, Working Draft Sequence, 26 unordered pieces. Accession AC168227 Mar. 2008. obtained from: http://www.ncbi.nlm.nih.gov/nuccore/AC168227[Mar. 5, 2013 7:42:44 AM], 51 pages.*
Bos taurus clone CH240-296E20, Working Draft Sequence, 11 unordered pieces. Accession AC218712. Mar. 2008. obtained from http://www.ncbi.nlm.nih.gov/nuccore/ac218712[Mar. 5, 2013 7:37:56 AM], 38 pages.*

\* cited by examiner

*Primary Examiner* — Juliet Switzer
(74) *Attorney, Agent, or Firm* — Kening Li; Pinsent Masons LLP

(57) ABSTRACT

A single nucleotide polymorphic site at position 59752 of the bovine PGR gene is associated with improved fertilization rate or early embryo survival. Disclosed are nucleic acid molecules, kits, methods of genotyping and marker assisted bovine breeding methods.

15 Claims, 2 Drawing Sheets

```
57001 gatgtgcttc acataaaaaa agcaggggca gggggaccgg tggagagaga attacccatg
57061 gcagattgta cagaaagtca agaaagagtc actgcactta agaacgaaga cattgttgat
57121 ggcattactc tgttttataa gcacagtgga catataagcc cagttccaat aagctgagga
57181 gtaaaggttg agatggttgg atggcatcac cgacatgagt ttgagcaaac tctgggagtt
57241 ggtgatggac agggaggtgt ggtgtgctgc agtccatggg gtcgcaaaga gtcagacatg
57301 actgagcgac tgaactgaac tgaaaagtaa aggaaactga tcaaaggctg taagtgcaga
57361 tgactttttc accaacttag ataacaaaga aagggatgaa gtcaaggaga attaagagtg
57421 agacacacag ttccgttttt ttttttttt tcttgattat ggaattttg aaatggaaaa
57481 gcttgaggag aaaagaagac atccttgaaa ggggagcaac tgaagatttt aggaggaaac
57541 tgatgggggaa ggtttgaaag caggtagaaa ggaatggttt tagcaacatg cagtgagtac
57601 cctctaatgg ggacatcttc tctgagacac tgaaggaggt gctattgtaa atcatttaga
57661 aacggaaaag agaccgctta gaagcattcc agctacagat ggttcaggct tttttcctgg
57721 atgtttttga cagaggagta tagagaagaa cagcctgccc ttaaacaagg gcagttacat
57781 ctctgagcac cgtttaagtg tgttctctag agagaataga aaaatcttgc tttctgttct
57841 ctcatgagaa atcagtgcag agtcaagata aattatcata aataaataga taaacttaca
57901 tacactttg ggcttctctg gtggctcaaa cagtaaagaa tcagcctgcg atgtgggaca
57961 cctaggttca atctctgggt caggaagatc ctctgggga ggatatggca accccctcca
58021 gtattcttgc ctggataatc ctcatggaca gaggagcctg gcgggctata ttccgtgggg
58081 tcgcaaagag tcgaacgcaa gtgagcgact aagcacagca caacacaaac acttttactc
58141 ccacagtcat tcctgtagcc tgaagaaaaa aaaaatatat atatgtatat ataaattaaa
58201 ccggagtcca attagaaagt agcatgcagt gcattccact aacctagagg gcatagttgt
58261 ggagcttcat aactgctctt tggagagggg caagggaacg agcaccagtg tgtgagagtg
58321 gtggtggtgg tttagtcact gagtgatgtc tgactcttgc aacccatgc cctgtacccc
58381 accggcctcc tctgtccatg cagttctcta ggccagaata ctggagtggg tagccgttcc
58441 cttctccagg agatcttcct gacccaggga tctaacccag gtctcctgca ttgcagggg
58501 attctttatc atctgagcca ccagggaagc ccagtatgtg agagtacatg aatagaagtt
58561 tgtggaggaa tctgttttgg agcaaagact atctgatttt ctaaaacgtc ccaggtcaag
58621 aatcattttg ttattagcta tctcataaaa cacggccttt gtgccattta tcgttgcagc
58681 gtagccttt cttgctcagt taaatacaca tttaagggat ctctgtgttc ctttactaca
58741 aactttggtt aaaaaaatgg atctgattt aatgtcaact aatacaaaat actgggcttc
58801 ctgggttctt cagtggtaaa gaatctacct gccaagcagg agaagtgggt tcactccctg
58861 ggtcaggaag atcctctgga aagggaatg gcgacaccct ccaatattct tgcctggaga
58921 atcccatggg cagaggagcc tgctgggctg cagtccttgg ggttgcaaaa cagtcagatg
58981 tgacttaaca agtaaacaac aatataaaat agtataggaa aattccatgg tattttaaaa
59041 ttgaaaattt caacttttaa aattattttt aagcaatctg atgatgttca aagtctcaca
59101 gtctatttca taggaattca atggaaaata agaagtgcca aagcagtaaa tattctagtt
59161 aatatttata tgtctaagct gacaattttt tcatttta tttaacctaa atagattgct
59221 ccatgcctta ttaaatataa catatttgg tttaaataat catcattgtt gaatattaaa
59281 ctttttccc agactttttg aagggtataa gtaaccactt atacaaaaac ccatcacaaa
59341 atgagcacag ggtcatgttt taccctcatt tcttctgtaa ttctctcctg tccttcactg
59401 agtttttctc attgttttaa attgctctca ctttatcatt atttctcccc atcctgtttt
59461 ctaattttag ccaagataaa caagacagta aagtcaatac aatcagtgat agttttaca
                                        PGRF4
59521 tgctattcaa gttcatgaga ttctttaaga gtgaatttgc tccaagattc tccaaaagaa
59581 ttaagcacat aggttttatt aaaaagtcta tcacagagac ttctttgtct atatctgttc
59641 tcttgaaggt ttatatgtta aaaagaaaag gttttactag aacttgacta tcttaacaca
59701 ctaatgctta tcagcaacat gtacctaatc ttgaaataat ggtgatctaa agacatggtg
59761 atctgctgac accattaata agatgcacag aaatatttta caaaagatgt ttaaaggagt
59821 tctggaatta gtttctaaga tgtgttcccc tcatttaggc tcctgaaggc agaggtttat
59881 tgcacaagtt tagagcatta caagcattca gctatgccaa gcaagaggcc agctgagaca
59941 gttatgctct tactaatgtg cacctctcct cttgtcactg cataagcttt ccagcagtct
60001 ttagatattt taaataattg ttccctaatt tttgtttgtt ttttaggaca gcataactac
60061 ttatgtgctg gaagaaacga ttgcattgtt gataaaatcc gcagaaaaa ctgcccagca
60121 tgtcgcctta gaaagtgctg tcaggctggc atggttcttg gaggtaatga tgatgttttc
60181 atcaataact gtctgatatt tatattaact aaattctgtc tgatgtttgt attataaaac
60241 catgggtcag aaaatcttag ttttcttatt tctatcttga ttattggtgt ctggatgaag
60301 cagctgatac cattttatta acactgtaga tttccagcag attgaagttt gttatagata
                                                    PGRR4
60361 cgtagtaaac ttcaatttgt ctatattgct tgtaagtaga tgttatggga aggtcgggct
60421 ttccaggtgg cgcagtggta aagaatccgc ctgccagtgc aggagatgca agagacacgg
```

FIGURE 1

```
60481 gttagatccc tgggtcagga agatacsctg gagtaggaaa tggcaacctg cccagtatgc
60541 ttgcttggga aattccatgg annnnnnnnn nnnnnnnnnn nnnnnnnnnn nnnnnnnnnn
60601 nnnnnnnnnn nngctccccac catgtggcct tgagtacatc accagcsctt tctgggcacc
60661 agtctctgtc tgcaaaatga gagcagtgaa gtctcttcca gctcaaatac tgattctgtg
60721 aactgaataa gtaccttaat ctccatcttt tcgtgcctcc atcaacccct cccttcgat
60781 gacccttcca cattctcttt aaataactga atattgagcc cttacactta ccaggtacta
60841 ttttaagttc tggagttcta cagtgagcaa aatggaccaa atctcagcct tcatggagct
60901 tacactctag gcagaggaga acaacacata tacatatata tatacacaca cacacacaca
60961 cacacacaca cacacacaca cacacacaaa agcagagaca ttactttgcc aacaaaggtc
61021 cgtctagtca aggctatggt ttttcctgtg gtcatgtatg gatgtaagag ttggactgtg
61081 aagaaagctg agcaccaaag aattgatgct tttgaactgt ggtgttggag aagactcttg
61141 agagtccctt ggactgcaag gagatccaac cagtccatcc taaaggagat cagccctggg
61201 atttctttgg aaggaatgat gctaaagctg aaattccagt actttggcca cctcatgcaa
61261 agagttgact cattggaaaa gactctaatg ctgggaggga ttggggtcag gaggagaagg
61321 ggatgacaga ggatgagatg gctggatggc atccccaact cgatggatgt gagtttgagt
61381 gaactccagg agttggtgat ggacagggag gcctggcgtg ctgcgattca tggggtctca
61441 aagagtggga cactaatgag tgactgaact gaactgatgt atatatatca agtgaagata
61501 aatattatgc agtgtattaa gcagggttca ttaatgggaa tctcagagag gggcttcact
61561 cctgaaccct ttactctgat taaaattttc attttagtca tttcctaagc agtaatatct
61621 ctaaaatcct gaatatgatg tagtagttct aattttttcta caacgagctt ttaaaattca
61681 tgatttattg aatacatatc taataaacca ccagccacag ttcatatacc ataaatggta
61741 tctgttacct tctgagaagg agtgtatgag accagcattt tttgactgct cactgtgtta
61801 agcaccctac ttagttctgt ctctacagcc tgtgaacatg tacagtctaa tccctaataa
61861 ataattgtta aacagaagag tgagtgattt aagagtggcg ccaaacatta ttatgcagat
61921 aaaacaaaag aatgaattaa ttctatctga gggagctggc aaaagcttct gagaggaggc
61981 tttcaaagaa tgaatacaaa tgttatcaat gaaaatggag aagagtattt acaatgaaaa
62041 acatgatgca ctgtagtgat gatttttctg gaaagtcagt tgtttagtgg gaacaacaag
62101 aaatgaagct tgaaagttac cttggcccag ctgggttctg gaggttgaac tctgttctgt
62161 atgcagtaga accagtgatc tttctaacaa actgtggacc atccatggaa tagagcccac
62221 atttctaagt gcagcacacc accccttttcc gcaccgagta actgccctct cttttttctaa
62281 gcccttctct caccagtcct gggggaaccc taccctccag tcaccaacac tcacctgtct
62341 ttgcacactt ttgattttttg cctgcattgt tcttaaactc cttgtgaact gttgtatttc
62401 cttcacatta agttcaagca tcatatttttt tgtgaaatct tcccatctgc atagtcactg
62461 cagagatagg ggtggggaca gttaaatgta gtgcttttca tgtctgggga ggctgagcgt
62521 ccttgagtca gcctggattg gaccttgcac taccgatact tacttctgca ttcctgccct
62581 tccaaggggga gactgaccca agtgggagtg atgagaccca gcagttcccc ctcatcccag
62641 cccacaggag ggactggaaa ttcacttttct ctctctcctc ccacagtttc ttgtatttac
62701 attcttcttt gtacttcctt cсttgttttta taactattta cttgtatccc attcaacgat
62761 ttctcctaat ccaagtttga gttgtttaca aacaggaatt tcattttagt gtttcagcac
62821 caaagtactt gtttaagaag tgctcactaa atatctgtga tgattattttt aaagtcagaa
62881 tctgcctacc aatgcaggag atatatgaga tactggtttg atccatgagt caggaagatc
62941 ccctggagaa ggaaatggca acccactctg gtagtctttt ttttttttaat ttatattttta
63001 ttgaagggta attgctttac agaattttgc tgttttctgt caaacctcaa ctcattattt
63061 gagaaatgca aatcaaaact acgatgaaat atcactctgg tattcttgcc tgaaaggtca
63121 catggacaga ggagcctggc aggctacagt ccatggggct gcaaagagtt ggacttgact
63181 ccgcacacaa cgtacttgca tgcattcttg aatataaggt ccaatgtagc cattactaga
63241 actcaagaaa gagtgattgg aagaggcaaa ggggatgtgg tttcatgtag tgttttttcat
63301 tttgaggaaa ggcgctagcc cttaagcagt cttccattcc ataactgaat ttatttttact
63361 ggtcttaact gttataatgg ataagtgatt taagatgaac tagtgtaaaa atgatgagac
63421 acctagccac tgagaaactt gagtttgttc agaagagaga tttgggggtt ccaaccagca
63481 acaaaataga tgctcagtaa gaaacagagt gatgaggaga agagaacttc agagaagact
63541 cggaaccagg atgcagggg agggttcgag tctaggggaca gagcgtaaag cagcatcaga
63601 gcagggtcag cagcaacaaa catccttgta cctgtgactt tgtgtgtacc aactgagaag
63661 tcctctaggc tgtatatcta gaaagctagt caatttctgg ttcactggga tattgtgtac
63721 ctttaaactt actgttacct aatcaccaaa ttaccctcca gcatctttgc ttctaccagt
63781 gtttgagagc tcttgttgtt atgatgttat gtatccttac ctgtgttttc agcctttttaa
63841 attcttctaa tttgatggtc ctaaaattta tatctaattt tgttttaatt tgtgtgtcct
63901 agattatggt gagagaaaat attgctatat ttcttggccg cttgtacttc ctgttctatg
63961 atttagctat ccatagttat tggccatttt tcaacagtat tgtctttttt gttactgatt
64021 gatacaactt acatctgtac tctcctaatt ctgtattagc tacatacaat ttatgtcttg
64081 acttttttacc ttgtttataa tatctttttt ctaattttta tatggtcata tgtgtcagta
64141 ttctcсctttt atgtttcttta gccctgaaat tgtatagata atttactgaa tatcatctaa
64201 actcttaaaa gtttattttt atattcaagt ccttaacttc cctacaagta tctttttttt
```

FIGURE 1

ASSOCIATION OF THE PROGESTERONE RECEPTOR WITH FERTILITY

CROSS REFERENCE TO RELATED APPLICATIONS

This application claims priority of U.S. App. Ser. No. 61/261,377, filed Nov. 16, 2009, the contents of which are incorporated herein by reference.

STATEMENT AS TO RIGHT TO INVENTIONS MADE UNDER FEDERALLY SPONSORED RESEARCH OR DEVELOPMENT

This invention was made with United States government support awarded by the following agencies: USDA/CS-REES12-CRHF-0-6055. The United States government has certain rights in the invention.

FIELD OF THE INVENTION

The present invention relates to a method of cattle genetic testing using molecular genetic methods by assaying for the presence of at least one genetic marker indicative of improved fertility. More specifically, the genetic marker relates to a single nucleotide polymorphism (SNP) found on the progesterone receptor gene.

BACKGROUND OF THE INVENTION

Dairy cows are significant investments for dairy farmers, and enormous efforts, such as animal breeding and artificial insemination, have been and continue to be invested in ensuring that the animals have high and sustained productivity, and that the milk produced are of high quality. Perhaps partially due to these breeding efforts for high productivity, fertility of the modern high-producing dairy cow has been decreasing for the last 30-50 years and has become a major concern of farmers and the dairy industry worldwide (Royal et al., 2000; Dobson et al., 2007; Dobson et al., 2008).

Previous studies have shown that a major subcomponent of infertility and higher incidence of late embryo mortality in dairy cattle is abnormal hormone activity causing different effects ranging from prolonged luteal activity to delayed ovulation (Lamming and Darwash 1998). However, recent studies have shown that low fertilization rates and embryonic loss—referring to death of embryos from the fertilization to completion of differentiation—seem to be the main factors contributing to infertility in dairy cattle (Santos et al., 2004; Morris and Diskin, 2008).

Although genetic factors are known to be involved in this decline of fertility (Royal et al., 2002), the discovery of specific genes has been challenging (Veerkamp and Beerda, 2007). The identification of genes with major effects on fertility would allow the implementation of gene-assisted selection to improve reproductive performance in dairy cows.

In addition, traditional breeding techniques involve the studying of sire progenies, and evaluating their traits including fertility or milk production ratings (transmitting abilities) to guide further breeding. This standard technique is time consuming and costly, requiring years to evaluate the true genetic value by progeny testing each bull. Many cows must be bred and give birth to offspring, and their fertility be measured, which may be inherently difficult. In case of mild production traits, the females must be raised, bred, allowed to give birth and finally milked for a length of time to measure their phenotypic traits.

Furthermore, selection based purely on phenotypic characteristics does not efficiently take into account genetic variability caused by complex gene action and interactions, and the effect of the environmental and developmental variants. There is thus a need for a method of genetically evaluating cattle to enable breeders to more accurately select animals at both the phenotypic and the genetic level.

Marker-assisted selection can lower the high cost of progeny testing currently used to improve sires, since young bull progeny could be evaluated immediately after birth, and young bulls that are determined by genetic testing to have undesirable markers would never be progeny tested or even prior to birth, for the presence/absence of the marker.

Thus, there is a need for the identification of genes with effects on fertility which would serve as genetic markers and allow the implementation of gene-assisted selection to improve reproductive performance in dairy cows.

SUMMARY OF THE INVENTION

The present inventor investigated the effects of PGR on dairy cattle fertilization rate or early embryo survival. In one embodiment, the present invention provides for an isolated nucleic acid molecule comprising a polymorphic site of position 59752 ("SNP 59752"; numbering is according to GenBank accession no. NC_007313, region 6406286.6522574) of SEQ ID NO: 1 and at least 9 contiguous nucleotides or bases of SEQ ID NO: 1 adjacent to the polymorphic site, wherein the nucleic acid molecule comprises an guanine (G) base at position 59752 of SEQ ID NO: 1. It is recognized that SEQ ID NO: 1 is already known, and the nucleic acid molecule therefore does not encompass one that consists of SEQ ID NO: 1.

Preferably, the nucleic acid molecule which comprises at least 10, at least 11, at least 12, at least 13, at least 14 or at least 15 nucleotides, more preferably at least 20, still more preferably at least 25, contiguous bases of SEQ ID NO: 1 adjacent to the polymorphic site. In one embodiment, the isolated nucleic acid molecule comprises not more than 1,500 nt, preferably not more than 1000 nt, more preferably not more than 900 nt, more preferably not more than 800 nt, more preferably not more than 700 nt, preferably not more than 600 nt, more preferably not more than 500 nt, preferably not more than 400 nt, more preferably not more than 300 nt, more preferably not more than 150 nt., preferably not more than 100 nt., still more preferably not more than 50 nt.

The nucleic acid molecule preferably contains the polymorphic site which is within 4 nucleotides of the center of the nucleic acid molecule. Preferably, the polymorphic site is at the center of the nucleic acid molecule.

In another embodiment, the nucleic acid molecule contains the polymorphic site which is at the 3'-end of the nucleic acid molecule.

The present invention also provides an array of nucleic acid molecules comprising at least two nucleic acid molecules described above.

The present invention further provides a kit comprising a nucleic acid molecule described above, and a suitable container.

Also provided is a method for detecting single nucleotide polymorphism (SNP) in bovine PGR gene, wherein the PGR gene has a nucleic acid sequence of SEQ ID NO: 1, the method comprising determining the identity of a nucleotide at position 59752, and comparing the identity to the nucleotide identity at a corresponding position of SEQ ID NO: 1.

In another embodiment, the present invention provides a method for genotyping a bovine cell, using the method above.

Suitable bovine cell may be an adult cell, an embryo cell, a sperm, an egg, a fertilized egg, or a zygote. The identity of the nucleotide may be determined by sequencing the PGR gene, or a relevant fragment thereof, isolated from the cell. The PGR gene or a relevant fragment thereof is isolated from the cell via amplification by the polymerase chain reaction (PCR) of genomic DNA of the cell, or by RT-PCR of the mRNA of the cell. Preferably, the PCR or RT-PCR is conducted with a pair of primers having the following sequences:

```
5' GTGAATTTGCTCCAAGATTC 3'    (SEQ ID NO: 2)
and

5' GCCCGACCTTCCCATAAC 3'      (SEQ ID NO: 3)
```

In a further embodiment, the present invention provides a method for progeny testing of cattle, the method comprising collecting a nucleic acid sample from the progeny, and genotyping said nucleic sample as described above.

Further provided is a method for selectively breeding of cattle using a multiple ovulation and embryo transfer procedure (MOET), the method comprising superovulating a female animal, collecting eggs from said superovulated female, in vitro fertilizing said eggs from a suitable male animal, implanting said fertilized eggs into other females allowing for an embryo to develop, genotyping the developing embryo, and terminating pregnancy if the developing embryo does not have guanine (G) at position 59752. Preferably, pregnancy is terminated if the embryo is homozygously A at position 59752.

In a preferred embodiment, the method is used for selectively breeding dairy cattle, comprising selecting a bull that is hemizygously or homozygously G at position 59752 of its PGR gene, and using its semen for fertilizing a female animal. Preferably the bull is homozygously G at position 59752. More preferably, the female animal is also hemizygously or homozygously G at position 59752, preferably homozygously G. MOET procedure may be preferably used for the selective breeding. It is recognized that for optimized embryo survival rate, a genotype of GG is preferred at position 59752, while for optimal fertilization rate, both GG and GC are preferred.

The present invention also provides a method for testing a dairy cattle for fertility, including fertilization rate or embryo survival, or both, comprising genotyping its cells, wherein a cattle being homozygously G at position 59752 indicates that the cattle has desirable fertility trait.

DESCRIPTION OF THE DRAWINGS

FIG. 1 shows a portion of the cattle PGR gene sequence (SEQ ID NO: 1) where the relevant polymorphic site is shown.

DETAILED DESCRIPTION OF THE INVENTION

In previous studies, the present inventor reported the associations between genotypes of ovaries and subsequent fertility data on their oocytes and embryos for the signal transducer and activator of transcription 5A (STAT5A) and the fibroblast growth factor 2 (FGF2) genes with fertility traits using an in vitro fertilization (IVF) experimental population (Khatib et al., 2008a, b). FGF2 and STAT5A were chosen as candidate genes because they are members of the interferon-tau and placental lactogen pathways which are known to be involved in the initiation and maintenance of pregnancy in ruminants (Spencer and Bazer, 2002).

Progesterone is a required hormone for pregnancy initiation, embryo implantation and development, which are mediated by the progesterone receptor (PGR) in mammals (McNeill et al., 2006). Indeed, several studies have shown that high as well as low concentrations of progesterone are associated with low embryonic survival (Reviewed in Morris and Diskin, 2008). Mann et al. (1999, 2006) reported that successful embryo development is contingent on sufficient levels of progesterone and that late or poor rise in progesterone levels during the luteal phase results in poorly developed embryos that are virtually incapable of secreting sufficient amounts of interferon-tau at a critical point of development.

Several research groups have examined whether PGR affects embryonic development and survival through direct action on embryos or through indirect effects of maternal factors produced in the reproductive tract (Hou and Gorski, 1993; Ying et al., 2000; Morris and Diskin, 2008). In order to affect fertilization rate, PGR must be expressed in either sperm or oocytes or both. Gene expression and immunocytochemistry analyses have shown that PGR was present in oocytes and in the 2-cell, and 4-cell stages of pig embryos, but was undetectable in the developmental stages after the 4-cell stage (Ying et al., 2000). Also, expression analysis of PGR in cumulus cells surrounding mature human oocytes revealed an important role of this gene in the regulation of oocyte maturation and embryo development (Hasegawa et al., 2005). Moreover, in a recent study, it was reported that after its activation in response to progesterone, PGR translocates to the nucleus where it binds the 3-casein promoter (Buser et al., 2007). The authors found that a mutual interference between PGR and STAT5A at the β-casein promoter has an important role in the repression of β-casein transcription during pregnancy.

Given that STAT5A has been found to affect fertilization rate and early embryonic survival and that PGR is a key gene in pregnancy and embryonic development, PGR was chosen as a candidate gene for its potential effects on fertility traits in cattle, with the objective of determining the association of the PGR gene variants with fertilization rate and early embryonic survival.

A single nucleotide polymorphism (SNP) of the progesterone receptor gene was found to have a significant association with fertility traits and early embryonic survival in Holstein cattle. Specifically, an in-vitro fertilization (IVF) system was utilized to maximize the efficiency of the identification of genetic factors affecting fertility. This IVF system would allow the assessment of fertilization and embryonic survival rates independent of influences from the uterine environment. A total of 5,566 fertilization attempts were performed and a total of 3,679 embryos were produced using oocytes from 324 Holstein cows and semen from 10 Holstein bulls. Sequencing of pooled DNA samples from ovaries revealed a SNP (G/C) in intron 3 of PGR. A generalized linear model was used to analyze the association of this SNP with fertilization and embryonic survival rates for each ovary. Oocytes obtained from CC ovaries showed a 61% fertilization rate vs. 68% and 69% for GC and GG ovaries, respectively (P=0.00039). The survival rate of embryos produced from GG ovaries was 5% and 6% higher than that of GC and CC ovaries (P=0.00036). These results indicate that the PGR SNP could be used in marker-assisted selection breeding programs in Holstein dairy cattle.

As used in the present disclosure, the term "polymorphism" refers to the occurrence of two or more alternative genomic sequences or alleles between or among different genomes or individuals. "Polymorphic" refers to the condition in which two or more variants of a specific genomic sequence can be found in a population. A "polymorphic site" is the locus at which the variation occurs. Polymorphisms generally have at least two alleles, each occurring at a significant frequency in a selected population. A polymorphic locus may be as small as one base pair. The first identified allelic form is arbitrarily designated as the reference form, and other allelic forms are designated as alternative or variant alleles. The allelic form occurring most frequently in a selected population is sometimes referred to as the wild type form. Diploid organisms may be homozygous or heterozygous for allelic forms. A biallelic polymorphism has two forms, and a triallelic polymorphism has three forms, and so on.

Polymorphisms may provide functional differences in the genetic sequence, through changes in the encoded polypeptide, changes in mRNA stability, binding of transcriptional and translation factors to the DNA or RNA, and the like. Polymorphisms are also used to detect genetic linkage to phenotypic variation.

One type of polymorphism, single nucleotide polymorphisms (SNPs), has gained wide use for the detection of genetic linkage recently. SNPs are generally biallelic systems, that is, there are two alleles that an individual may have for any particular SNP marker. In the instant case, the SNP is used for determining the genotypes of the PGR gene, which is found to have strong correlation to fertility traits.

The provided sequences also encompass the complementary sequence corresponding to any of the provided polymorphisms. In order to provide an unambiguous identification of the specific site of a polymorphism, the numbering of the original PGR sequence in the GenBank (GenBank accession no. NC_007313, region 6406286.6522574) is shown in FIG. 1 and is used. One C/G SNP was detected in the ovaries at position 59752 in intron 3 of PGR.

The present invention provides nucleic acid based genetic markers for identifying bovine animals with superior fertility traits. In general, for use as markers, nucleic acid fragments, preferably DNA fragments, will be of at least 9, 10, 11, or 12 nucleotides (nt), preferably at least 15 nt, usually at least 20 nt, often at least 50 nt. Such small DNA fragments are useful as primers for the polymerase chain reaction (PCR), and probes for hybridization screening, etc.

The term primer refers to a single-stranded oligonucleotide capable of acting as a point of initiation of template-directed DNA synthesis under appropriate conditions (i.e., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer but typically ranges from 15 to 30 nucleotides. Short primer molecules generally require cooler temperatures to form sufficiently stable hybrid complexes with the template. A primer need not reflect the exact sequence of the template but must be sufficiently complementary to hybridize with a template. The term primer site, or priming site, refers to the area of the target DNA to which a primer hybridizes. The term primer pair means a set of primers including a 5' upstream primer that hybridizes with the 5' end of the DNA sequence to be amplified and a 3', downstream primer that hybridizes with the complement of the 3' end of the sequence to be amplified.

The term "probe" or "hybridization probe" denotes a defined nucleic acid segment (or nucleotide analog segment) which can be used to identify by hybridization a specific polynucleotide sequence present in samples, said nucleic acid segment comprising a nucleotide sequence complementary of the specific polynucleotide sequence to be identified.

"Probes" or "hybridization probes" are nucleic acids capable of binding in a base-specific manner to a complementary strand of nucleic acid.

An objective of the present invention is to determine which embodiment of the polymorphisms a specific sample of DNA has. For example, it is desirable to determine whether the nucleotide at a particular position is A or C. An oligonucleotide probe can be used for such purpose. Preferably, the oligonucleotide probe will have a detectable label, and contains an A at the corresponding position. Experimental conditions can be chosen such that if the sample DNA contains an A, they hybridization signal can be detected because the probe hybridizes to the corresponding complementary DNA strand in the sample, while if the sample DNA contains a G, no hybridization signal is detected.

Similarly, PCR primers and conditions can be devised, whereby the oligonucleotide is used as one of the PCR primers, for analyzing nucleic acids for the presence of a specific sequence. These may be direct amplification of the genomic DNA, or RT-PCR amplification of the mRNA transcript of the PGR gene. The use of the polymerase chain reaction is described in Saiki et al. (1985) Science 230:1350-1354. Amplification may be used to determine whether a polymorphism is present, by using a primer that is specific for the polymorphism. Alternatively, various methods are known in the art that utilize oligonucleotide ligation as a means of detecting polymorphisms, for examples see Riley et al (1990) Nucleic Acids Res. 18:2887-2890; and Delahunty et al (1996) Am. J. Hum. Genet. 58:1239-1246. The detection method may also be based on direct DNA sequencing, or hybridization, or a combination thereof. Where large amounts of DNA are available, genomic DNA is used directly. Alternatively, the region of interest is cloned into a suitable vector and grown in sufficient quantity for analysis. The nucleic acid may be amplified by PCR, to provide sufficient amounts for analysis.

Hybridization may be performed in solution, or such hybridization may be performed when either the oligonucleotide probe or the target polynucleotide is covalently or non-covalently affixed to a solid support. Attachment may be mediated, for example, by antibody-antigen interactions, poly-L-Lys, streptavidin or avidin-biotin, salt bridges, hydrophobic interactions, chemical linkages, UV cross-linking baking, etc. Oligonucleotides may be synthesized directly on the solid support or attached to the solid support subsequent to synthesis. Solid-supports suitable for use in detection methods of the invention include substrates made of silicon, glass, plastic, paper and the like, which may be formed, for example, into wells (as in 96-well plates), slides, sheets, membranes, fibers, chips, dishes, and beads. The solid support may be treated, coated or derivatized to facilitate the immobilization of the allele-specific oligonucleotide or target nucleic acid. For screening purposes, hybridization probes of the polymorphic sequences may be used where both forms are present, either in separate reactions, spatially separated on a solid phase matrix, or labeled such that they can be distinguished from each other.

Hybridization may also be performed with nucleic acid arrays and subarrays such as described in WO 95/11995. The arrays would contain a battery of allele-specific oligonucleotides representing each of the polymorphic sites. One or both polymorphic forms may be present in the array, for example the polymorphism of position 59752 may be represented by either, or both, of the listed nucleotides. Usually such an array will include at least 2 different polymorphic sequences, i.e. polymorphisms located at unique positions within the locus, and may include all of the provided polymorphisms. Arrays of interest may further comprise sequences, including polymorphisms, of other genetic sequences, particularly other sequences of interest. The oligonucleotide sequence on the array will usually be at least about 12 nt in length, may be the length of the provided polymorphic sequences, or may extend into the flanking regions to generate fragments of 100 to 200 nt in length. For examples of arrays, see Ramsay (1998) Nat. Biotech. 16:4044; Hacia et al. (1996) Nature Genetics 14:441-447; Lockhart et al. (1996) Nature Biotechnol. 14:1675-1680; and De Risi et al. (1996) Nature Genetics 14:457-460.

The identity of polymorphisms may also be determined using a mismatch detection technique, including but not limited to the RNase protection method using riboprobes (Winter et al., Proc. Natl. Acad. Sci. USA 82:7575, 1985; Meyers et al., Science 230:1242, 1985) and proteins which recognize nucleotide mismatches, such as the *E. coli* mutS protein (Modrich, P. Ann. Rev. Genet. 25:229-253, 1991). Alternatively, variant alleles can be identified by single strand conformation polymorphism (SSCP) analysis (Orita et al., Genomics 5:874-879, 1989; Humphries et al., in Molecular Diagnosis of Genetic Diseases, R. Elles, ed., pp. 321-340, 1996) or denaturing gradient gel electrophoresis (DGGE) (Wartell et al., Nucl. Acids Res. 18:2699-2706, 1990; Sheffield et al., Proc. Natl. Acad. Sci. USA 86:232-236, 1989).

A polymerase-mediated primer extension method may also be used to identify the polymorphism(s). Several such methods have been described in the patent and scientific literature and include the "Genetic Bit Analysis" method (WO92/15712) and the ligase/polymerase mediated genetic bit analysis (U.S. Pat. No. 5,679,524). Related methods are disclosed in WO91/02087, WO90/09455, WO95/17676, U.S. Pat. Nos. 5,302,509, and 5,945,283. Extended primers containing a polymorphism may be detected by mass spectrometry as described in U.S. Pat. No. 5,605,798. Another primer extension method is allele-specific PCR (Ruao et al., Nucl. Acids Res. 17:8392, 1989; Ruao et al., Nucl. Acids Res. 19, 6877-6882, 1991; WO 93/22456; Turki et al., J. Clin. Invest. 95:1635-1641, 1995). In addition, multiple polymorphic sites may be investigated by simultaneously amplifying multiple regions of the nucleic acid using sets of allele-specific primers as described in Wallace et al. (WO 89/10414).

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}$P, $^{35}$S, $^{3}$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

It is readily recognized by those ordinarily skilled in the art that in order to maximize the signal to noise ratio, in probe hybridization detection procedure, the polymorphic site should at the center of the probe fragment used, whereby a mismatch has a maximum effect on destabilizing the hybrid molecule; and in a PCR detection procedure, the polymorphic site should be placed at the very 3'-end of the primer, whereby a mismatch has the maximum effect on preventing a chain elongation reaction by the DNA polymerase. The location of nucleotides in a polynucleotide with respect to the center of the polynucleotide are described herein in the following manner. When a polynucleotide has an odd number of nucleotides, the nucleotide at an equal distance from the 3' and 5' ends of the polynucleotide is considered to be "at the center" of the polynucleotide, and any nucleotide immediately adjacent to the nucleotide at the center, or the nucleotide at the center itself is considered to be "within 1 nucleotide of the center." With an odd number of nucleotides in a polynucleotide any of the five nucleotides positions in the middle of the polynucleotide would be considered to be within 2 nucleotides of the center, and so on. When a polynucleotide has an even number of nucleotides, there would be a bond and not a nucleotide at the center of the polynucleotide. Thus, either of the two central nucleotides would be considered to be "within 1 nucleotide of the center" and any of the four nucleotides in the middle of the polynucleotide would be considered to be "within 2 nucleotides of the center," and so on.

In some embodiments, a composition contains two or more differently labeled oligonucleotides for simultaneously probing the identity of nucleotides or nucleotide pairs at two or more polymorphic sites. It is also contemplated that primer compositions may contain two or more sets of allele-specific primer pairs to allow simultaneous targeting and amplification of two or more regions containing a polymorphic site.

A diverse range of SNP genotyping methods are known to those skilled in the art and may be used for the purposes of the present invention. These methods include hybridization-based methods, such as Dynamic allele-specific hybridization (DASH) (see e.g. Howell et al. Nat. Biotechnol. 17:87-8); detection through molecular beacons (Abravaya et al., 2003, Clin Chem Lab Med. 41:468-474); and high density oligonucleotide SNP arrays (Rapley R., Harbron S. (Eds.) (2004) Molecular Analysis and Genome Discovery. Chichester. John Wiley & Sons Ltd.). Enzyme-based methods use a broad range of enzymes including DNA ligase, DNA polymerase and nucleases. These methods include: restriction fragment length polymorphism (RFLP); PCR-based methods, such as Tetra-primer ARMS-PCR (Nucleic Acids Res. 2001, 29: e88); Flap endonuclease (FEN) based Invader Assay (Olivier, 2005, Mutat Res. 573:103-10); the Primer Extension (including MALDI-TOF Mass spectrometry and ELISA-like methods (Rapley & Harbron 2004, supra); Taqman assay (McGuigan & Ralston, 2002, Psychiatr Genet. 12:133-6); oligonucleotide ligase assay (Rapley & Harbron 2004). Several other methods based on physical properties of DNA are also available such as Single strand conformation polymorphism (Costabile et al. 2006 Hum Mutat. 27:1163-73); Temperature gradient gel electrophoresis (TGGE) (Rapley & Harbron 2004); denaturing high performance liquid chromatography (Oefner & Underhill 1995, Am J Hum Genet. 57, A266), and High Resolution Melting analysis.

Alternatively, the relevant portion of the PGR gene of the sample of interest may be amplified via PCR and directly sequenced, and the sequence be compared to the wild type sequence shown in FIG. 1. It is readily recognized that, other than those disclosed specifically herein, numerous primers can be devised to achieve the objectives. PCR and sequencing techniques are well known in the art and reagents and equipments are readily available commercially.

DNA markers have several advantages; segregation is easy to measure and is unambiguous, and DNA markers are co-dominant, i.e., heterozygous and homozygous animals can be distinctively identified. Once a marker system is established selection decisions could be made very easily, since DNA markers can be assayed any time after a blood sample can be collected from the individual infant animal, or even earlier by testing embryos in vitro if very early embryos are collected. The use of marker assisted genetic selection will greatly facilitate and speed up cattle breeding problems. For example, a modification of the multiple ovulation and embryo transfer (MOET) procedure can be used with genetic marker technology. Specifically, females are superovulated, eggs are collected, in vitro fertilized using semen from superior males and implanted into other females allowing for use of the superior genetics of the female (as well as the male) without having to wait for her to give birth to one calf at a time. Developing blastomeres at the 4-8 cell stage may be assayed for presence of the marker, and selection decisions made accordingly.

In one embodiment of the invention an assay is provided for detection of presence of a desirable genotype using the markers.

The term "genotype" as used herein refers to the identity of the alleles present in an individual or a sample. In the context of the present invention a genotype preferably refers to the description of the polymorphic alleles present in an individual or a sample. The term "genotyping" a sample or an individual for a polymorphic marker refers to determining the specific allele or the specific nucleotide carried by an individual at a polymorphic marker.

The present invention is suitable for identifying a bovine, including a young or adult bovine animal, an embryo, a semen sample, an egg, a fertilized egg, or a zygote, or other cell or tissue sample therefrom, to determine whether said bovine possesses the desired genotypes of the present invention, some of which are indicative of improved fertility (fertilization rate or early embryo survival).

Further provided is a method for genotyping the bovine PGR gene, comprising determining for the two copies of the PGR gene present the identity of the nucleotide pair at position 59752.

One embodiment of a genotyping method of the invention involves examining both copies of the PGR gene, or a fragment thereof, to identify the nucleotide pair at the polymorphic site in the two copies to assign a genotype to the individual. In some embodiments, "examining a gene" may include examining one or more of: DNA containing the gene, mRNA transcripts thereof, or cDNA copies thereof. As will be readily understood by the skilled artisan, the two "copies" of a gene, mRNA or cDNA, or fragment thereof in an individual may be the same allele or may be different alleles. In another embodiment, a genotyping method of the invention comprises determining the identity of the nucleotide pair at the polymorphic site.

The present invention further provides a kit for genotyping a bovine sample, the kit comprising in a container a nucleic acid molecule, as described above, designed for detecting the polymorphism, and optionally at least another component for carrying out such detection. Preferably, a kit comprises at least two oligonucleotides packaged in the same or separate containers. The kit may also contain other components such as hybridization buffer (where the oligonucleotides are to be used as a probe) packaged in a separate container. Alternatively, where the oligonucleotides are to be used to amplify a target region, the kit may contain, preferably packaged in separate containers, a polymerase and a reaction buffer optimized for primer extension mediated by the polymerase, such as PCR.

In one embodiment the present invention provides a breeding method whereby genotyping as described above is conducted on bovine embryos, and based on the results, certain cattle are either selected or dropped out of the breeding program.

Through use of the linked marker loci, procedures termed "marker assisted selection" (MAS) may be used for genetic improvement within a breeding nucleus; or "marker assisted introgression" for transferring useful alleles from a resource population to a breeding nucleus (Soller, M. 1990) Genetic mapping of the bovine genome using DNA-level markers with particular attention to loci affecting quantitative traits of economic importance. J. Dairy Sci. 73:2628-2646; Soller, M. (1994) Marker-assisted selection, an overview. Anim. Biotech. 5:193-208).

In summary, based on the positional, functional, and regulatory information, PGR gene was chosen as a candidate gene for investigation of association with fertility and early embryonic survival traits. We identified SNP59752, a C/G SNP in the ovaries at position 59752 in intron 3 of PGR, which can be used in marker assisted selection programs in dairy cattle.

The following examples are intended to illustrate preferred embodiments of the invention and should not be interpreted to limit the scope of the invention as defined in the claims.

EXAMPLES

DNA was extracted from ovaries and semen samples using phenol/chloroform standard protocols. In order to detect single nucleotide polymorphisms (SNP) in PGR, 3 pooled ovary DNA samples were amplified using different pairs of primers. Amplification and SNP identification were as described in Khatib et al. (2008a, b). One C/G SNP was detected in the ovaries at position 59752 in intron 3 of PGR (GenBank accession no. NC_007313, region 6406286.6522574). For genotyping of ovaries, the primers PGRF4 5' GTGAATTTGCTCCAAGATTC 3' (SEQ ID NO: 2) and PGRR45' GCCCGACCTTCCCATAAC 3' (SEQ ID NO: 3) were used to amplify an 869-bp fragment. The PCR products were digested with the restriction enzyme AdeI and electrophoresed on a 2.0% agarose gel.

Association of PGR variants in ovaries with fertilization and survival rates was analyzed using a generalized linear model methodology (McCullagh and Nelder, 1989) for binary outcomes using the following logistic regression model:

$$\log\left(\frac{p_i}{1-p_i}\right) = \mu + Bull_{(i)} + STAT5A_{(i)} + FGF2_{(i)} + PGR_{(i)},$$

where $p_i$ is the survival rate of embryos produced from the ith ovary (i=1, 2, . . . n), which has been fertilized with semen from the bull $Bull_{(i)}$ (10 different bulls were used), and has the genotypes $STAT5A_{(i)}$ for a STAT5A SNP (Khatib et al., 2008a), $FGF2_{(i)}$ for a FGF2 SNP (Khatib et al., 2008b) and $PGR_{(i)}$ for the PGR SNP in this study; STAT5A and FGF2 are included in the model because they showed significant association with survival rate (Khatib et al., 2008a, b). Similarly, fertilization rate was modeled with STAT5A and PGR but not FGF2 because it was not significant (Khatib et al., 2008b) for this trait. A likelihood ratio test was applied to assess the significance of the PGR SNP effect in the model. The analysis was performed using R with functions from the base packages (R Development Core Team 2008). The GG, GC, and CC genotypic frequencies in ovaries were 0.37, 0.48, and 0.15, respectively, and frequencies of alleles G and C were 0.61 and 0.39, respectively. The fertilization rate of oocytes from CC ovaries was 61% compared to 68% and 69% those obtained from GC and GG ovaries, respectively (P=0.00039) (Table 2). Since the oocytes cannot be used for DNA extraction and genotyping (as they are needed for the IVF process), the ovaries from which these oocytes were collected must be genotyped. Then associations between genotypes of ovaries for PGR and fertilization and survival rates were performed. Thus, genotypes of ovaries represent genotypes of oocytes used in the fertilization process. Furthermore, it has been determined that the early stages of mammalian development are dependent on transcripts and proteins present in the oocytes (Zuccotti et al., 2008), thus making the female gamete important in the current study.

The survival rate of embryos produced from GG ovaries was 36% compared to 31% and 30% produced from GC and CC ovaries (P=0.00034), respectively (Table 2). Hou and Gorski (1993) reported the expression of PGR in mouse embryos at the blastocyst stage. The authors concluded that progesterone and PGR are both crucial for embryonic survival. Thus, our results on the association of PGR with fertilization and survival rates of embryos supports the hypothesis of Hou and Gorski (1993) that PGR acts directly in embryos and that it may have a significant impact on early embryonic development.

TABLE 1

The number[1] of ovaries and oocytes used in the fertilization and the average number of oocytes and embryos per ovary and standard deviation (SD)

| Bull | No. of ovaries | No. of oocytes | Oocytes/ovary (SD) | No. of embryos | Embryos/ovary (SD) |
|---|---|---|---|---|---|
| 1 | 94 | 1259 | 13.4 (8.94) | 842 | 9.0 (6.89) |
| 2 | 58 | 606 | 10.4 (7.74) | 428 | 7.4 (5.35) |
| 3 | 20 | 330 | 16.5 (7.04) | 179 | 9.0 (4.74) |
| 4 | 20 | 263 | 13.2 (8.54) | 121 | 6.1 (4.37) |
| 5 | 40 | 543 | 13.6 (7.49) | 349 | 8.7 (6.37) |
| 6 | 67 | 568 | 8.5 (5.05) | 417 | 6.2 (4.13) |
| 7 | 67 | 581 | 8.7 (4.6) | 430 | 6.4 (4.10) |
| 8 | 68 | 744 | 10.9 (7.46) | 517 | 7.6 (5.74) |
| 9 | 89 | 1343 | 15.1 (10.76) | 905 | 10.2 (7.88) |
| 10 | 66 | 1196 | 18.1 (15.80) | 849 | 12.9 (14.38) |

[1]Numbers include all ovaries collected and all embryos produced.

TABLE 2

Number of fertilization attempts and embryos of each genotypic class, the observed fertilization rate (FR) and embryonic survival rate (SR), and the association test between PGR variants and fertility traits.

| Ovary genotype | No. of ovaries[1] | No. of fertilizations | Observed FR | No. of embryos | Observed SR |
|---|---|---|---|---|---|
| GG | 121 | 2,005 | 0.69 | 1331 | 0.36 |
| GC | 155 | 2,721 | 0.68 | 1832 | 0.31 |
| CC | 48 | 840 | 0.61 | 516 | 0.30 |
| Total | 324 | 5566 | | 3679 | |
| Association test (P value) | | | 0.00039 | | 0.00036 |

[1]Numbers of successfully genotyped and having more than 4 oocytes per fertilization Even though there was a lack of pedigree information because ovaries were collected from a slaughterhouse, the large number of farms represented in the slaughterhouse and the length of collection time (about 3 years) make it reasonable to assume that cows were not related.

Given that the GG genotype was found to be associated with both fertilization and survival rates, PGR could be used in gene-assisted selection breeding programs in dairy cattle to improve fertility.

REFERENCES CITED

Buser, A. C., E. K. Gass-Handel, S. L. Wyszomierski, W. Doppler, S. A. Leonhardt, J. Schaack, J. M. Rosen, H. Watkin, S. M. Anderson, and D. P. Edwards. 2007. Progesterone receptor repression of prolactin/signal transducer and activator of transcription 5-mediated transcription of the beta-casein gene in mammary epithelial cells. Mol. Endocrinol. 21:106-125.

Dobson, H., R. Smith, M. Royal, Ch. Knight, I. Sheldon. 2007. The high producing dairy cow and its reproductive performance. Reprod. Domest. Anim 20.17-23.

Dobson, H., S. L. Walker, M. J. Morris, J. E. Routly, and R. F. Smith. 2008. Why is it getting more difficult to successfully artificially inseminate dairy cows? Animal 2:1104-1111.

Gadkar, S., C. A. Shah, G. Sachdeva, U. Samant, and C. P. Puri. 2002. Progesterone receptor as an indicator of sperm function. Biol. Reprod. 67:1327-1336.

Hasegawa, J., A. Yanaihara, S. Iwasaki, Y. Otsuka, M. Negishi, T. Akahane, and T. Okai. 2005. Reduction of progesterone receptor expression in human cumulus cells at the time of oocyte collection during IVF is associated with good embryo quality. Hum. Reprod. 20:2194-2200.

Hou, Q., and J. Gorski. 1993. Estrogen receptor and progesterone receptor genes are expressed differentially in mouse embryos during preimplantation development. Proc. Natl. Acad. Sci. USA. 90:9460-9464.

Khatib, H., R. L. Monson, V. Schutzkus, D. M. Kohl, G. J. M. Rosa, and J. J. Rutledge. 2008a. Mutations in the STAT5A Gene are Associated with Embryonic Survival and Milk Composition in Cattle. J. Dairy Sci. 91:784-793.

Khatib, H., C. Maltecca, R. L. Monson, V. Schutzkus, X. Wang, and J. J. Rutledge. 2008b. The fibroblast growth factor 2 gene is associated with embryonic mortality in cattle. J. Anim Sci. 86:2063-2067.

Lamming, G. E., and A. O. Darwash. 1998. The use of milk progesterone profiles to characterise components of subfertility in milked dairy cows. Anim Reprod. Sci. 52:175-190.

Mann G. E., G. E. Lamming, R. S. Robinsson, and D. C. Wathes. 1999. The regulation of interferon-tau production and uterine hormone receptors during early pregnancy. J. Reprod. Fertil. Suppl. 54:317-328.

Mann G. E., M. D. Fray, and G. E. Lamming 2006. Effects of time of progesterone supplementation on embryo development and interferon-tau production in the cow. Vet. J. 171: 500-503.

McCullagh, P. and J. A. Nelder. 1989. Generalized Linear Models. 2nd ed. London: Chapman and Hall.

McNeill R. E., J. M. Sreenan, M. G. Diskin, M. T. Cairns, R. Fitzpatrick, T. J. Smith, D. G. Morris. 2006. Effect of systemic progesterone concentration on the expression of progesterone-responsive genes in the bovine endometrium during the early luteal phase. Reprod. Fertil. Dev. 18:573-583.

Morris, D., and M. Diskin. 2008. Effect of progesterone on embryo survival. Animal 2:1112-1119.

R Development Core Team (2008). R: A language and environment for statistical computing. R Foundation for Statistical Computing, Vienna, Austria. ISBN 3-900051-07-0, URL http://www.R-project.org.

Royal, M. D., J. E. Pryce, J. A. Woolliams, and A. P. Flint. 2002. The genetic relationship between commencement of luteal activity and calving interval, body condition score, production, and linear type traits in Holstein-Friesian dairy cattle. J. Dairy Sci. 85:3071-3080.

Royal, M., G. E. Mann, and A. P. Flint. 2000. Strategies for reversing the trend towards subfertility in dairy cattle. Vet. J. 160:53-60.

Santos, J. E. P., W. W. Thatcher, R. C. Chebel, R. L. A. Cerri, and K. N. Galvao. 2004. The effect of embryonic death rates in cattle on the efficacy of estrus synchronization programs. Anim Reprod. Sci. 83:513-535.

Spencer, T. E., and F. W. Bazer. 2002. Biology of progesterone action during pregnancy recognition and maintenance of pregnancy. Front. Biosci. 7:d1879-1898.

Veerkamp, R. F., and B. Beerda. 2007. Genetics and genomics to improve fertility in high producing dairy cows. Theriogenology 68S:S266-S273.

Wu, J. T., P. S. Tsai, S. L. Lee, and F. P. Cheng. 2005. Characterization of the progesterone receptor on canine spermatozoa. Reprod. Fertil. Dev. 17:733-741.

Ying, C., Y. C. Yang, W. F. Hong, W. T. Cheng, and W. L. Hsu. 2000. Progesterone receptor gene expression in preimplantation pig embryos. Eur. J. Endocrinol. 143:697-703.

Zuccotti, M., V. Merico, L. Sacchi, M. Bellone, T. C. Brink, R. Bellazzi, M. Stephanelli, C. A. Redi, S. Garagna, and J. Adjaye. 2008. Maternal Oct-4 is a potential key regulator of the developmental competence of mouse oocytes. BMC Dev. Biol. 8:97.

What is claimed is:

1. A dairy cattle breeding method for desirable fertilization rate or early embryo survival rate, or both, the method comprising detecting a guanine at a nucleotide of the PGR gene of a dairy cattle cell or tissue corresponding to position 2752 of SEQ ID NO: 1, and using said cell or tissue for breeding purposes.

2. A method according to claim 1, wherein the dairy cattle cell is an adult cell, an embryo cell, a sperm, an egg, a fertilized egg, or a zygote.

3. A method according to claim 1, wherein the identity of the nucleotide is determined by sequencing the PGR gene, or a relevant fragment thereof, isolated from the cell or tissue.

4. A method according to claim 3, wherein the PGR gene or a relevant fragment thereof is isolated from the cell or tissue via amplification by the polymerase chain reaction (PCR) of genomic DNA of the cell or tissue.

5. A method according to claim 3, wherein the identity of the position on both copies of the gene in the cell or tissue are determined.

6. A method for selectively breeding of cattle the method comprising superovulating a female animal, collecting eggs from said superovulated female, in vitro fertilizing said eggs with semen from a suitable male animal, culturing said fertilized eggs into developing embryos, determining the identity of a nucleotide of the PGR gene of a developing embryo corresponding to position 2752 of SEQ ID NO: 1, and planting a developing embryo into a suitable female only if the PRG gene of the developing embryo has G at the position of the PGR gene corresponding to position 2752 of SEQ ID NO: 1.

7. A method according to claim 6, wherein a developing embryo is planted into a suitable female only if the developing embryo is homozygously G at the position corresponding to position 2752 of SEQ ID NO: 1.

8. A method for selectively breeding dairy cattle, comprising selecting a bull that is homozygously G at a position of the PGR gene corresponding to position 2752 of SEQ ID NO: 1 and using its semen for fertilizing a female animal.

9. A method according to claim 8, wherein the female animal is in vitro fertilized.

10. A method according to claim 8, wherein MOET procedure is used.

11. A method according to claim 8, wherein said female animal is also homozygously G at the position of the PGR gene corresponding to position 2752 of SEQ ID NO: 1.

12. A method for selectively breeding dairy cattle for desirable fertilization rate or early embryo survival rate, or both, comprising selecting a female animal whose PRG gene is homozygously guanine at a position corresponding to position 2752 of SEQ ID NO: 1, and fertilizing eggs from the female animal with semen from a suitable bull.

13. A method according to claim 12, wherein the female animal is in vitro fertilized.

14. A method according to claim 12, wherein MOET procedure is used.

15. A method according to claim 12, wherein said the PRG gene of the bull is also homozygously guanine at a position corresponding to position 2752 of SEQ ID NO: 1.

* * * * *

SEQUENCE LISTING

```
<160> NUMBER OF SEQ ID NOS: 3

<210> SEQ ID NO 1
<211> LENGTH: 7261
<212> TYPE: DNA
<213> ORGANISM: Bos taurus
<220> FEATURE:
<221> NAME/KEY: misc_feature
<222> LOCATION: (3562)..(3612)
<223> OTHER INFORMATION: n is a, c, g, or t

<400> SEQUENCE: 1
gatgtgcttc acataaaaaa agcaggggca gggggaccgg tggagagaga attacccatg      60
gcagattgta cagaaagtca agaaagagtc actgcactta agaacgaaga cattgttgat     120
ggcattactc tgtttttataa gcacagtgga catataagcc cagttccaat aagctgagga    180
gtaaaggttg agatggttgg atggcatcac cgacatgagt ttgagcaaac tctgggagtt     240
ggtgatggac agggaggtgt ggtgtgctgc agtccatggg gtcgcaaaga gtcagacatg     300
actgagcgac tgaactgaac tgaaaagtaa aggaaactga tcaaaggctg taagtgcaga     360
tgactttttc accaacttag ataacaaaga aagggatgaa gtcaaggaga attaagagtg     420
agacacacag ttccgttttt tttttttttt tcttgattat ggaattttttg aaatggaaaa    480 gcttgaggag aaaagaagac atccttgaaa ggggagcaac tgaagatttt aggaggaaac     540 tgatgggaa ggtttgaaag caggtagaaa ggaatggttt tagcaacatg cagtgagtac      600
cctctaatgg ggacatcttc tctgagacac tgaaggaggt gctattgtaa atcatttaga     660
aacggaaaag agaccgctta gaagcattcc agctacagat ggttcaggct ttttttcctgg    720 atgttttttga cagaggagta tagagaagaa cagcctgccc ttaaacaagg gcagttacat    780
ctctgagcac cgtttaagtg tgttctctag agagaataga aaaatcttgc tttctgttct     840
ctcatgaaaa atcagtgcag agtcaagata aattatcata aataaataga taaacttaca    900
tacacttttg ggcttctctg gtggctcaaa cagtaaagaa tcagcctgcg atgtgggaca     960
cctaggttca atctctgggt caggaagatc ctctggggga ggatatggca accccctcca    1020
gtattcttgc ctggataatc ctcatggaca gaggagcctg gcgggctata ttccgtgggg    1080
tcgcaaagag tcgaacgcaa gtgagcgact aagcacagca caacacaaac acttttactc    1140
ccacagtcat tcctgtagcc tgaagaaaaa aaaaatatat atatgtatat ataaattaaa    1200
ccggagtcca attagaaagt agcatgcagt gcattccact aacctagagg gcatagttgt    1260
ggagcttcat aactgctctt tggagagggg caagggaacg agcaccagtg tgtgagagtg    1320
gtggtggtgg tttagtcact gagtgatgtc tgactcttgc aaccccatgc cctgtacccc    1380
```

```
accggcctcc tctgtccatg cagttctcta ggccagaata ctggagtggg tagccgttcc    1440
cttctccagg agatcttcct gacccaggga tctaacccag gtctcctgca ttgcaggggg    1500
attctttatc atctgagcca ccagggaagc ccagtatgtg agagtacatg aatagaagtt    1560
tgtggaggaa tctgttttgg agcaaagact atctgatttt ctaaaacgtc ccaggtcaag    1620
aatcattttg ttattagcta tctcataaaa cacggccttt gtgccattta tcgttgcagc    1680 gtagccttt  cttgctcagt taaatacaca tttaagggat ctctgtgttc ctttactaca    1740
aactttggtt aaaaaaatgg atctgatttt aatgtcaact aatacaaaat actgggcttc    1800
ctgggttctt cagtggtaaa gaatctacct gccaagcagg agaagtgggt tcactccctg    1860
ggtcaggaag atcctctgga aaagggaatg gcgacaccct ccaatattct tgcctggaga    1920
atcccatggg cagaggagcc tgctgggctg cagtccttgg ggttgcaaaa cagtcagatg    1980
tgacttaaca agtaaacaac aatataaaat agtataggaa aattccatgg tattttaaaa    2040
ttgaaaattt caacttttaa aattattttt aagcaatctg atgatgttca aagtctcaca    2100
gtctatttca taggaattca atggaaaata agaagtgcca aagcagtaaa tattctagtt    2160
aatatttata tgtctaagct gacaatttt  ttcattttta tttaacctaa atagattgct    2220
ccatgcctta ttaaatataa catattttgg tttaaataat catcattgtt gaatattaaa    2280
cttttttccc agacttttg  aagggtataa gtaaccactt atacaaaaac ccatcacaaa    2340
atgagcacag ggtcatgttt taccctcatt tcttctgtaa ttctctcctg tccttcactg    2400 agttttctc  attgttttaa attgctctca ctttatcatt atttctcccc atcctgtttt    2460
ctaattttag ccaagataaa caagacagta aagtcaatac aatcagtgat agtttttaca    2520
tgctattcaa gttcatgaga ttctttaaga gtgaatttgc tccaagattc tccaaaagaa    2580
ttaagcacat aggttttatt aaaaagtcta tcacagagac ttctttgtct atatctgttc    2640
tcttgaaggt ttatatgtta aaagaaaag  gttttactag aacttgacta tcttaacaca    2700
ctaatgctta tcagcaacat gtacctaatc ttgaaataat ggtgatctaa agacatggtg    2760
atctgctgac accattaata agatgcacag aaatatttta caaaagatgt ttaaaggagt    2820
tctggaatta gtttctaaga tgtgttcccc tcatttaggc tcctgaaggc agaggtttat    2880
tgcacaagtt tagagcatta caagcattca gctatgccaa gcaagaggcc agctgagaca    2940
gttatgctct tactaatgtg cacctctcct cttgtcactg cataagcttt ccagcagtct    3000
ttagatattt taataattg  ttccctaatt tttgtttgtt ttttaggaca gcataactac    3060
ttatgtgctg gaagaaacga ttgcattgtt gataaaatcc gcagaaaaa  ctgcccagca    3120 tgtcgcctta gaaagtgctg tcaggctggc atggttcttg gaggtaatga tgatgttttc    3180
atcaataact gtctgatatt tatattaact aaattctgtc tgatgtttgt attataaaac    3240
catgggtcag aaaatcttag ttttcttatt tctatcttga ttattggtgt ctggatgaag    3300
cagctgatac catttattta acactgtaga tttccagcag attgaagttt gttatagata    3360
cgtagtaaac ttcaatttgt ctatattgct tgtaagtaga tgttatggga aggtcgggct    3420
ttccaggtgg cgcagtggta agaatccgc  ctgccagtgc aggagatgca agagacacgg    3480
gttagatccc tgggtcagga agataccctg gagtaggaaa tggcaacctg cccagtatgc    3540
ttgcttggga aattccatgg annnnnnnnn nnnnnnnnnn nnnnnnnnnn nnnnnnnnnn    3600
nnnnnnnnnn nngctcccca ccatgtggcc ttgagtacat caccagccct ttctgggcac    3660
cagtctctgt ctgcaaaatg agagcagtga agtctcttcc agctcaaata ctgattctgt    3720
gaactgaata agtaccttaa tctccatctt ttcgtgcctc catcaacccc tccctttcga    3780
```

```
tgacccttcc acattctctt taaataactg aatattgagc ccttacactt accaggtact    3840
attttaagtt ctggagttct acagtgagca aaatggacca aatctcagcc ttcatggagc    3900
ttacactcta ggcagaggag aacaacacat atacatatat atatacacac acacacacac    3960
acacacacac acacacacac acacacacaa aagcagagac attactttgc caacaaaggt    4020
ccgtctagtc aaggctatgg ttttcctgt ggtcatgtat ggatgtaaga gttggactgt     4080
gaagaaagct gagcaccaaa gaattgatgc ttttgaactg tggtgttgga aagactctt     4140 gagagtccct tggactgcaa ggagatccaa ccagtccatc ctaaaggaga tcagccctgg    4200
gatttctttg gaaggaatga tgctaaagct gaaattccag tactttggcc acctcatgca    4260
aagagttgac tcattggaaa agactctaat gctgggaggg attggggtca ggaggagaag    4320
gggatgacag aggatgagat ggctggatgg catccccaac tcgatggatg tgagtttgag    4380
tgaactccag gagttggtga tggacaggga ggcctggcgt gctgcgattc atggggtctc    4440
aaagagtggg acactaatga gtgactgaac tgaactgatg tatatatatc aagtgaagat    4500
aaatattatg cagtgtatta agcagggttc attaatggga atctcagaga ggggcttcac    4560
tcctgaaccc tttactctga ttaaaatttt cattttagtc atttcctaag cagtaatatc    4620
tctaaaatcc tgaatatgat gtagtagttc taattttct acaacgagct tttaaaattc     4680
atgatttatt gaatacatat ctaataaacc accagccaca gttcatatac cataaatggt    4740
atctgttacc ttctgagaag gagtgtatga gaccagcatt ttttgactgc tcactgtgtt    4800
aagcacccta cttagttctg tctctacagc ctgtgaacat gtacagtcta atccctaata    4860
aataattgtt aaacagaaga gtgagtgatt taagagtggc gccaaacatt attatgcaga    4920
taaaacaaaa gaatgaatta attctatctg agggagctgg caaaagcttc tgagaggagg    4980 cttttcaaaga atgaatacaa atgttatcaa tgaaaatgga gaagagtatt tacaatgaaa   5040
aacatgatgc actgtagtga tgattttct ggaaagtcag ttgtttagtg ggaacaacaa     5100
gaaatgaagc ttgaaagtta ccttggccca gctgggttct ggaggttgaa ctctgttctg    5160
tatgcagtag aaccagtgat cttctaaca aactgtggac catccatgga atagagccca     5220
catttctaag tgcagcacac caccccttc cgcaccgagt aactgccctc tcttttcta     5280 agcccttctc tcaccagtcc tgggggaacc ctaccctcca gtcaccaaca ctcacctgtc    5340
tttgcacact tttgatttt gcctgcattg ttcttaaact ccttgtgaac tgttgtattt     5400
ccttcacatt aagttcaagc atcatatttt ttgtgaaatc ttcccatctg catagtcact    5460
gcagagatag gggtggggac agttaaatgt agtgcttttc atgtctgggg aggctgagcg    5520
tccttgagtc agcctggatt ggaccttgca ctaccgatac ttacttctgc attcctgccc    5580
ttccaagggg agactgaccc aagtgggagt gatgagaccc agcagttccc cctcatccca    5640
gcccacagga gggactggaa attcactttc tctctctcct cccacagttt cttgtattta    5700
cattcttctt tgtacttcct tccttgtttt ataactattt acttgtatcc cattcaacga    5760
tttctcctaa tccaagtttg agttgttac aaacaggaat ttcatttag tgtttcagca      5820 ccaaagtact tgtttaagaa gtgctcacta aatatctgtg atgattattt taaagtcaga    5880
atctgcctac caatgcagga gatatatgag atactggttt gatccatgag tcaggaagat    5940
cccctggaga aggaaatggc aacccactct ggtagtcttt tttttttaa tttatatttt     6000 attgaagggt aattgcttta cagaattttg ctgttttctg tcaaacctca actcattatt    6060
tgagaaatgc aaatcaaaac tacgatgaaa tatcactctg gtattcttgc ctgaaaggtc    6120
acatggacag aggagcctgg caggctacag tccatggggc tgcaaagagt tggacttgac    6180
```

```
tccgcacaca acgtacttgc atgcattctt gaatataagg tccaatgtag ccattactag    6240
aactcaagaa agagtgattg gaagaggcaa aggggatgtg gtttcatgta gtgtttttca    6300
ttttgaggaa aggcgctagc ccttaagcag tcttccattc cataactgaa tttatttac     6360 tggtcttaac tgttataatg gataagtgat ttaagatgaa ctagtgtaaa aatgatgaga    6420
cacctagcca ctgagaaact tgagtttgtt cagaagagag atttgggggt tccaaccagc    6480
aacaaaatag atgctcagta agaaacagag tgatgaggag aagagaactt cagagaagac    6540
tcggaaccag gatgcagggg gagggttcga gtctagggac agagcgtaaa gcagcatcag    6600
agcagggtca gcagcaacaa acatccttgt acctgtgact ttgtgtgtac caactgagaa    6660
gtcctctagg ctgtatatct agaaagctag tcaatttctg gttcactggg atattgtgta    6720
cctttaaact tactgttacc taatcaccaa attaccctcc agcatctttg cttctaccag    6780
tgtttgagag ctcttgttgt tatgatgtta tgtatcctta cctgtgtttt cagcctttta    6840
aattcttcta atttgatggt cctaaaattt atatctaatt ttgttttaat ttgtgtgtcc    6900
tagattatgg tgagagaaaa tattgctata tttcttggcc gcttgtactt cctgttctat    6960
gatttagcta tccatagtta ttggccattt ttcaacagta ttgtcttttt tgttactgat    7020
tgatacaact tacatctgta ctctcctaat tctgtattag ctacatacaa tttatgtctt    7080 gacttttac cttgtttata atatcttttt tctaattttt atatggtcat atgtgtcagt     7140
attctcsctt tatgtttctt agccctgaaa ttgtatagat aatttactga atatcatcta    7200
aactcttaaa agtttatttt tatattcaag tccttaactt ccctacaagt atcttttttt    7260
t                                                                    7261

<210> SEQ ID NO 2
<211> LENGTH: 20
<212> TYPE: DNA
<213> ORGANISM: Bos taurus

<400> SEQUENCE: 2
gtgaatttgc tccaagattc                                                  20

<210> SEQ ID NO 3
<211> LENGTH: 18
<212> TYPE: DNA
<213> ORGANISM: Bos taurus

<400> SEQUENCE: 3
gcccgacctt cccataac                                                    18
```